(12) United States Patent
D'Urso et al.

(10) Patent No.: US 8,241,508 B2
(45) Date of Patent: Aug. 14, 2012

(54) METHOD OF FORMING COMPOSITE, ORDERED MATERIAL HAVING SHARP SURFACE FEATURES

(75) Inventors: Brian R D'Urso, Clinton, TN (US); John T Simpson, Clinton, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 388 days.

(21) Appl. No.: 11/463,940

(22) Filed: Aug. 11, 2006

(65) Prior Publication Data

US 2006/0289380 A1 Dec. 28, 2006

Related U.S. Application Data

(62) Division of application No. 10/900,248, filed on Jul. 27, 2004, now Pat. No. 7,150,904.

(51) Int. Cl.
*C25F 3/00* (2006.01)
(52) U.S. Cl. .......................................................... 216/11
(58) Field of Classification Search ................ 216/2, 11, 216/97; 65/411, 439, 429, 427, 409, 408
See application file for complete search history.

(56) References Cited

U.S. PATENT DOCUMENTS

| | | | | |
|---|---|---|---|---|
| 3,265,480 A | * | 8/1966 | Hicks, Jr. ........................ | 65/445 |
| 3,275,428 A | * | 9/1966 | Siegmund ....................... | 65/393 |
| 3,284,332 A | * | 11/1966 | Gladrow et al. .............. | 204/284 |
| 3,586,895 A | * | 6/1971 | Sowers et al. ................. | 313/524 |
| 5,234,594 A | | 8/1993 | Tonucci | |
| 5,493,169 A | | 2/1996 | Pierle | |
| 5,498,258 A | * | 3/1996 | Hakky et al. ..................... | 606/15 |
| 5,633,972 A | * | 5/1997 | Walt et al. ...................... | 385/116 |
| 5,863,449 A | * | 1/1999 | Grabbe ............................ | 216/24 |
| 5,928,525 A | * | 7/1999 | Ohtsu et al. ..................... | 216/24 |
| 6,256,533 B1 | * | 7/2001 | Yuzhakov et al. .............. | 604/21 |
| 6,503,231 B1 | * | 1/2003 | Prausnitz et al. .............. | 604/272 |
| 6,511,463 B1 | * | 1/2003 | Wood et al. .................... | 604/272 |
| 6,551,849 B1 | * | 4/2003 | Kenney .......................... | 438/34 |
| 6,660,363 B1 | | 12/2003 | Barthlott | |
| 2002/0138049 A1 | * | 9/2002 | Allen et al. .................... | 604/272 |
| 2002/0142150 A1 | | 10/2002 | Baumann | |
| 2002/0151245 A1 | | 10/2002 | Hofmann | |
| 2003/0104693 A1 | * | 6/2003 | Siegel et al. .................. | 438/680 |
| 2004/0063100 A1 | * | 4/2004 | Wang ............................... | 435/6 |
| 2004/0094503 A1 | * | 5/2004 | Ozeryansky .................... | 216/2 |
| 2005/0013536 A1 | * | 1/2005 | Walt ................................ | 385/27 |

OTHER PUBLICATIONS

McAllister, Devin et al. "Microfabricated Needles for Transdermal Delivery of Macromolecules and Nanoparticles: Fabrication Methods and Transport Studies" PNAS v100, No. 24, Nov. 25, 2003, pp. 13755-13760. Published onlie on Nov. 17, 2003.*

(Continued)

*Primary Examiner* — Nathan Empie
(74) *Attorney, Agent, or Firm* — Novak Druce + Quigg LLP

(57) ABSTRACT

A method of making a composite material having sharp surface features includes the steps of: making a composite body comprised of a recessive phase and a protrusive phase, the recessive phase having a higher susceptibility to a preselected etchant than the protrusive phase; and treating a surface of the composite body with the preselected etchant so that the protrusive phase protrudes from the surface to form a sharp surface feature, and the recessive phase defines a recessed surface area between the surface features.

24 Claims, 18 Drawing Sheets

OTHER PUBLICATIONS

S.A. McAuley, et al., "Silicon Micromachining Using a High-Density Plasma Source," Institute of Physics Publishing, 2001, pp. 2769-2774, vol. 34.

E.A. Litvinova, "Tunable Superhydrophobic Surfaces Fabricated by Nanosphere Lithography," MRS Bulletin, 2004, pp. 229-230.

J. Kim, et al., "Nanostructured Surfaces for Dramatic Reduction of Flow Resistance in Droplet-Based Microfluidics," IEEE, 2002, pp. 479-482.

T.N. Krupenkin, et al., "From Rolling Ball to Complete Wetting: The Dynamic Tuning of Liquids on Nanostructured Surafaces," Langmuir, 2004, pp. 3824-3827, vol. 20.

R. J. Tonucci, et al., "Nanochannel Array Glass," Science, 1992, pp. 783-785, vol. 258.

H.Y. Erbil, et al., "Transformation of a Simple Plastic into a Superhydrophobic Surface," Science, 2003, pp. 1377-1380, vol. 299.

* cited by examiner

METHOD OF FORMING COMPOSITE, ORDERED MATERIAL HAVING SHARP SURFACE FEATURES The United States Government has rights in this invention pursuant to contract no. DE-AC05-00OR22725 between the United States Department of Energy and UT-Battelle, LLC.

CROSS-REFERENCE TO RELATED APPLICATION

This patent application is related to another patent application by D'Urso and Simpson entitled "Composite, Nano-structured, Super-Hydrophobic Material" and filed on even date herewith, issued on Dec. 19, 2006 as U.S. Pat. No. 7,150,904, the entire disclosure of which is incorporated herein by reference.

FIELD OF THE INVENTION

The present invention relates to methods of making composite materials, and more particularly to differentially etched, ordered materials having sharp surface features. The invention further relates to super-hydrophobic surfaces, and more particularly to differentially etched, ordered, sharp-featured, super-hydrophobic surfaces.

BACKGROUND OF THE INVENTION

Hydrophobic surfaces bind very weakly with water, which makes drops of water "bead up" on the surface. A hydrophobic surface is generally defined and defined herein as that which has a contact angle greater than 900 with a drop of water. Hydrophobic materials include many well-known, commercially available polymers.

A super-hydrophobic surface is generally defined and defined herein as that which has a contact angle greater than 150° with a drop of water. The lotus leaf surface is known to be naturally super-hydrophobic due to the texture of its waxy surface.

New materials are and methods are being sought that provide capability for making sharp-featured surfaces that are especially suitable for super-hydrophobic applications.

In typical microfabrication and nanofabrication etching processes, care is taken to produce structures with steep sidewalls and/or high aspect ratios. Vacuum etching processes are used because the use of liquid chemical etchants typically results in rounded structures. Even in the process for producing microchannel or nanochannel glass, the materials and etchant are chosen to result in steep sidewalls and extremely high aspect ratios. In the present invention, a novel etching process is used to make structures with intentionally angled sidewalls, resulting in sharpened surface features. The novel process may produce atomically sharp points with a simple, robust process. This is in strong contrast to the usual rounded "wet" etched features or the precise timing and conditions typically needed for vacuum processing.

OBJECTS OF THE INVENTION

Accordingly, objects of the present invention include: the provision of a composite, differentially etched, ordered, material having sharp surface features, and also a composite, differentially etched, ordered, super-hydrophobic material. Further and other objects of the present invention will become apparent from the description contained herein.

SUMMARY OF THE INVENTION

In accordance with one aspect of the present invention, the foregoing and other objects are achieved by a composite material having sharp surface features including a recessive phase and a protrusive phase, the recessive phase having a higher susceptibility to a preselected etchant than the protrusive phase, the composite material having an etched surface wherein the protrusive phase protrudes from the surface to form a sharp surface feature.

In accordance with another aspect of the present invention, a spiked article including a composite material having sharp surface features including a recessive phase and a protrusive phase, the recessive phase having a higher susceptibility to a preselected etchant than the protrusive phase, the composite material having an etched surface wherein the protrusive phase protrudes from the surface to form a sharp surface feature.

In accordance with a further aspect of the present invention, a method of making a composite material having sharp surface features includes the steps of: making a composite body comprised of a recessive phase and a protrusive phase, the recessive phase having a higher susceptibility to a preselected etchant than the protrusive phase; and treating a surface of the composite body with the preselected etchant so that the protrusive phase protrudes from the surface to form a sharp surface feature, and the recessive phase defines a recessed surface area between the surface features.

Figure 2:
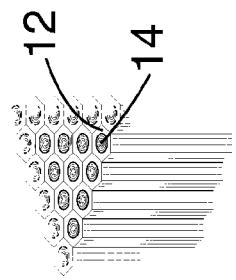
FIG. 2 is a schematic oblique view of the portion of a bundle of composite rods shown in FIG. 1 after heating, drawing and cutting in accordance with the present invention.

Several elements that are essentially the same across multiple figs. are assigned like call-out numerals.

For a better understanding of the present invention, together with other and further objects, advantages and capabilities thereof, reference is made to the following disclosure and appended claims in connection with the above-described drawings.

DETAILED DESCRIPTION OF THE INVENTION

The present invention is based upon a composite structure including a recessive phase material and a protrusive phase material. The respective phases provide differential etchability/solubility, the recessive phase having a greater etchability/solubility than the protrusive phase. By subjecting the surface of the composite structure to an etchant/solvent that removes more of the recessive phase than the protrusive phase, some of the protrusive phase forms sharp, protrusive surface features. The phrase "sharp surface feature" is defined herein to mean a generally tapered, protrusive structure that preferably terminates in a sharp terminus, ideally an atomically sharp point or ridge. "Sharp surface feature" can therefore refer to a feature having a base portion having a first cross sectional area, and a tip portion opposite the base portion having a reduced cross sectional area that is no more than 30% of the first cross sectional area, such as 25%, 20%, 15%, 10%, 8%, 6%, 5%, 4%, 3%, 2%, 1%, or less than 1% of the first cross sectional area. The reduction in cross sectional area in traversing from the base portion to the tip portion is preferably monotonic.

Sharp surface features include, for example, protrusions such as spikes and/or ridges. The protrusive phase is sharpened because even the protrusive phase is etched in the process, just more slowly than the recessive phase. The use of any differentially etchable/soluble recessive and protrusive materials in any combination to produce the desired effect is considered to fall within the scope of the present invention. Moreover, there are no limits to the variations of sizes and shapes of the sharp surface features. The composite base material may be made from any materials differentially etchable by any known etching method or methods.

The composite base material may be made from any materials which have suitable differential etching characteristics. Suitable materials include, for example, glasses, metals (including alloys), ceramics, polymers, resins, and the like. Choices of materials can have an effect on properties of the product, such as, for example, chemical resistance, ease and/or need of coating, strength, toughness, flexibility, elasticity, plasticity, etc.

The etchant, can comprise an: organic or inorganic acid or alkali; polar, nonpolar, organic, inorganic, or mixed solvent; or mixtures of any of the foregoing. The etchant is preselected to differentially etch the composite material as described herein. For example, an acid such as HF, HCl, HBr, or HI might be selected to differentially etch glass compositions.

The etchant can be a "mixed etchant system" which is comprised of a mixture of a plurality of etchants that give different etch contrast ratios when applied to the composite surface. For example, one etchant can preferentially etch one phase while the other etchant can preferentially etch the other phase. A mixed etchant system can be particularly useful because the contrast ratio of the etching process can be modified by changing the composition and/or relative concentrations of the etchants. An example of a mixed etchant system is a mixture of HF and HCl. The possible compositions of suitable mixed etchant systems are virtually without limits.

Moreover, a plurality of etchants can be used in a series of two or more sequential etching steps. For example, HF is applied to the composite surface in a first etching step, rinsed away, and then HCl is applied to the composite surface in a second etching step. The possible combinations of suitable etchants and etching steps are virtually without limits.

The method by which the etching is carried out is not critical to the invention, as long as the desired surface feature is achieved. For example, other, non-solution etching techniques may be used, such as plasma etching or other isotropic etch techniques.

The spiked composite material can be manufactured in a manner analogous to the process for making the well-known microchannel or nanochannel glass.

Figure 1:
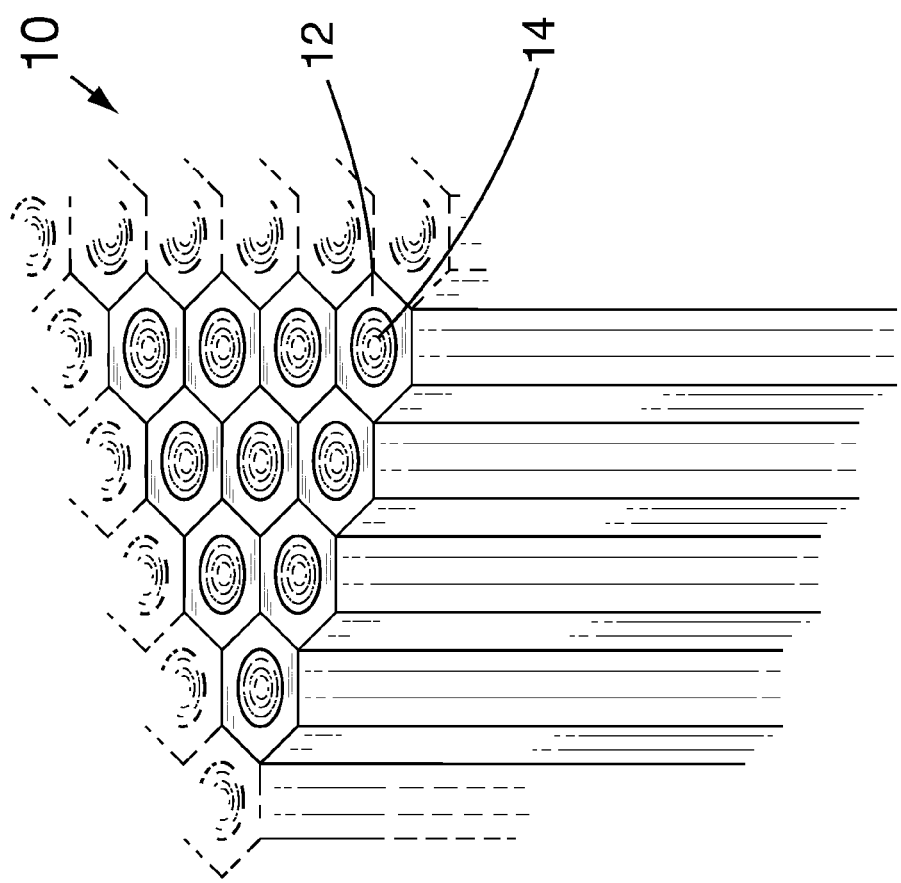
FIG. 1 is a schematic oblique view of a portion of a bundle of composite rods in accordance with the present invention.

Referring to FIG. 1, composite rods having a core 14 of a different material than the matrix material 12 are bundled in an aligned array, or bundle 10. The rod (matrix material) 12 preferably has a hexagonal or other outer cross-sectional shape to minimize voids while the core material 14 preferably has a circular cross-section, although neither of these parameters is considered to be critical to the invention. It may be advantageous for economical manufacturing for the matrix material 12 to have a circular cross-section. In this case the voids are filled in during subsequent processing. With round rods 12, the spacing of the core material 14 will be somewhat less precise.

The matrix material 12 and core material 14 are preferably selected based on differential etchability (susceptibility to etching or dissolution). (In the case of the nano-channel glass, the core glass has a much higher etchability than that of the matrix glass.) In the case of the previously unknown spiked surface of the present invention, the core material 14 has a lower etchability than the matrix material 12, and forms protrusive, sharp features upon etching of the composite surface.

It should be noted that the use of immiscible components in the composite may improve the ease of drawing the material. In general it may be advantageous to choose materials with specific miscibility to facilitate drawing without too much interdiffusion of the materials (excessively miscible) and without either component breaking up into droplets (insufficiently miscible).

The bundle 10 can heated to a temperature sufficient to soften the materials comprising the bundle 10, but low enough to avoid damage, decomposition, or other deleterious changes. The bundle 10 is then drawn along the axis of the bundled rods to fuse and reduce the diameter of the bundle 10. As shown in FIG. 2, the drawn bundle 20 has reduced size material rod matrix material 12 and respective core material 14. The drawn bundle 20 is cut transversely into sections which can be re-bundled to increase the number of core material 14 cores in the cross-section thereof.

Figure 3:
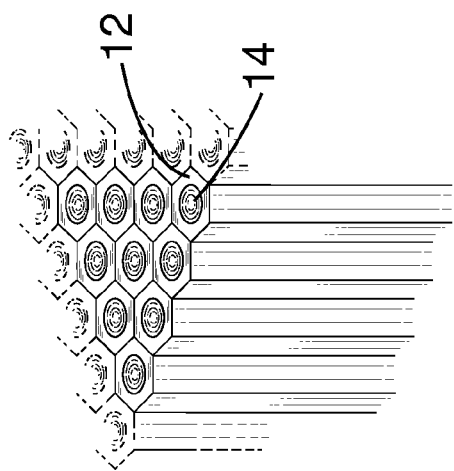
FIG. 3 is a schematic oblique view of the portion of a bundle of composite rods shown in FIG. 2 after re-bundling, re-drawing and cutting in accordance with the present invention.

The bundle 20 can then be drawn again. As shown in FIG. 3, the twice-drawn bundle 30 has further reduced size material rod matrix material 12 and respective core material 14. The twice-drawn bundle 30 is again cut transversely into sections which are re-bundled to further increase the number of core material 14 cores in the cross-section thereof.

The process of bundling, drawing, and cutting can be performed a single time or repeated many times until the desired diameter and spacing of the core material 14 is obtained. Core material 14 diameters and spacing on the nanometer scale is possible. The sizes of bundles and the number of rods contained therein can be varied throughout the process as desired.

Figure 4:
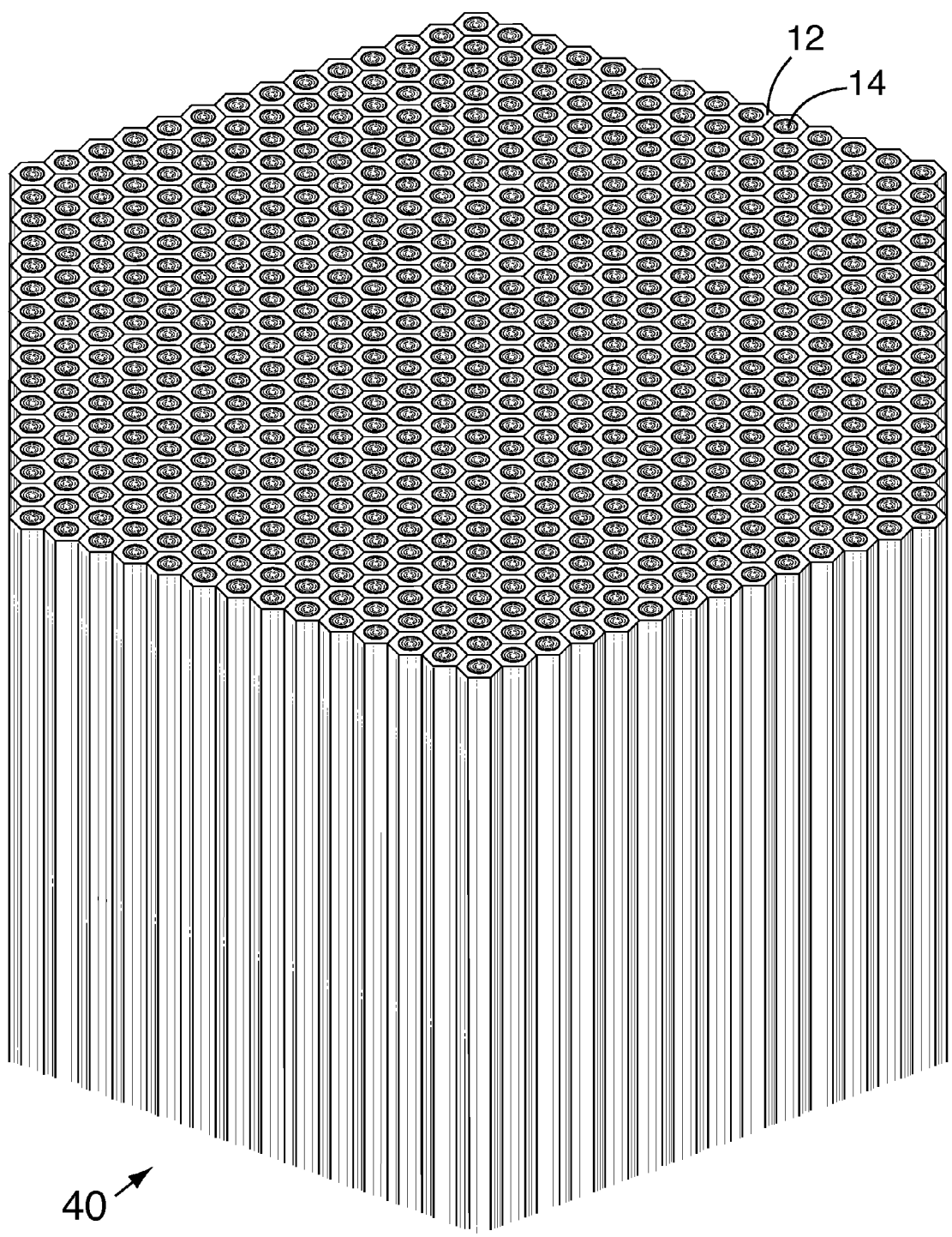
FIG. 4 is a schematic oblique view of the bundle of composite rods shown in FIG. 3 after re-bundling and fusing in accordance with the present invention.
Figure 5:
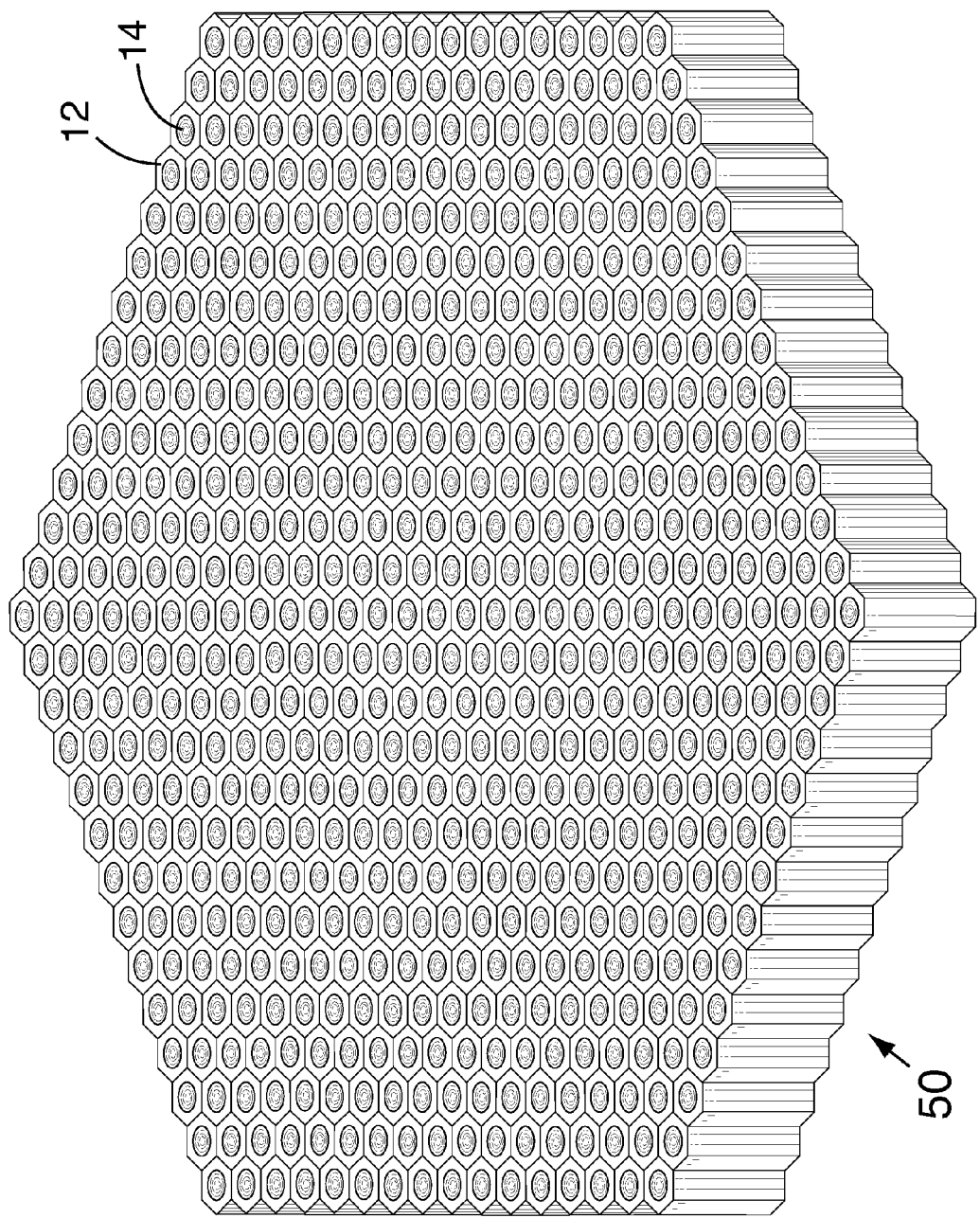
FIG. 5 is a schematic oblique view of a plate cut from the fused bundle of composite rods shown in FIG. 4 in accordance with the present invention.

After the final draw (which can be the first draw), the bundle can be cut, bundled, and fused in order to obtain a larger diameter boule. FIG. 4 schematically shows a representative portion of a boule 40. The boule 40 can be transversely cut to produce slices (plates, tiles) of any desired thickness. FIG. 5 schematically shows a representative portion of a plate 50. The cut is usually (but not necessarily) perpendicular to the original rods 12 and the drawing direction. One or both cut faces may be polished. Although a hexagonal boule 40 is shown and described as an example, a boule of any desired geometric shape can be formed, processed, and used in carrying out any of the various embodiments of the present invention.

Subsequently, one or both of the cut (composite) surfaces of the plate 50 is etched to create an array of spikes of core material 14 on one or both sides of the plate 50. The composite surface can be contacted with an etchant, (HF, for example), which etches the matrix material 12 (recessive phase) faster than the core material 14 (protrusive phase). The etching continues until the matrix material 12 is etched back to the desired depth, leaving some of the core material 14 protruding from the surface. The result is that the core material 14 is sharpened to a cone-shaped spike, the aspect ratio of the spike being dependent on the ratio of the matrix material 12 and core material 14 etching rates.

EXAMPLE I

In accordance with the present invention, glass rods having a Sylvania SG12™ (equivalent to Corning 0120™) core glass as the less etchable protrusive phase and Corning 8161™ cladding (matrix glass) as the more etchable recessive phase were bundled, heated to a temperature sufficient to soften the rods, and drawn to reduce the diameter thereof. The resulting rod was cut into sections that were re-bundled and redrawn. The above process was repeated until the diameter of the core glass was reduced to 5 µm and spaced apart about 7 µm. The rod was cut into sections, bundled, and fused to form a shorter, thicker rod having a diameter of about 1.5 cm. A thin plate was cut transversely from the end of the rod, polished, and subject to etching with HF at room temperature for a period of 20 min. to produce a spiked surface on the disk. The spikes were about 12 µm tall.

Figure 6:
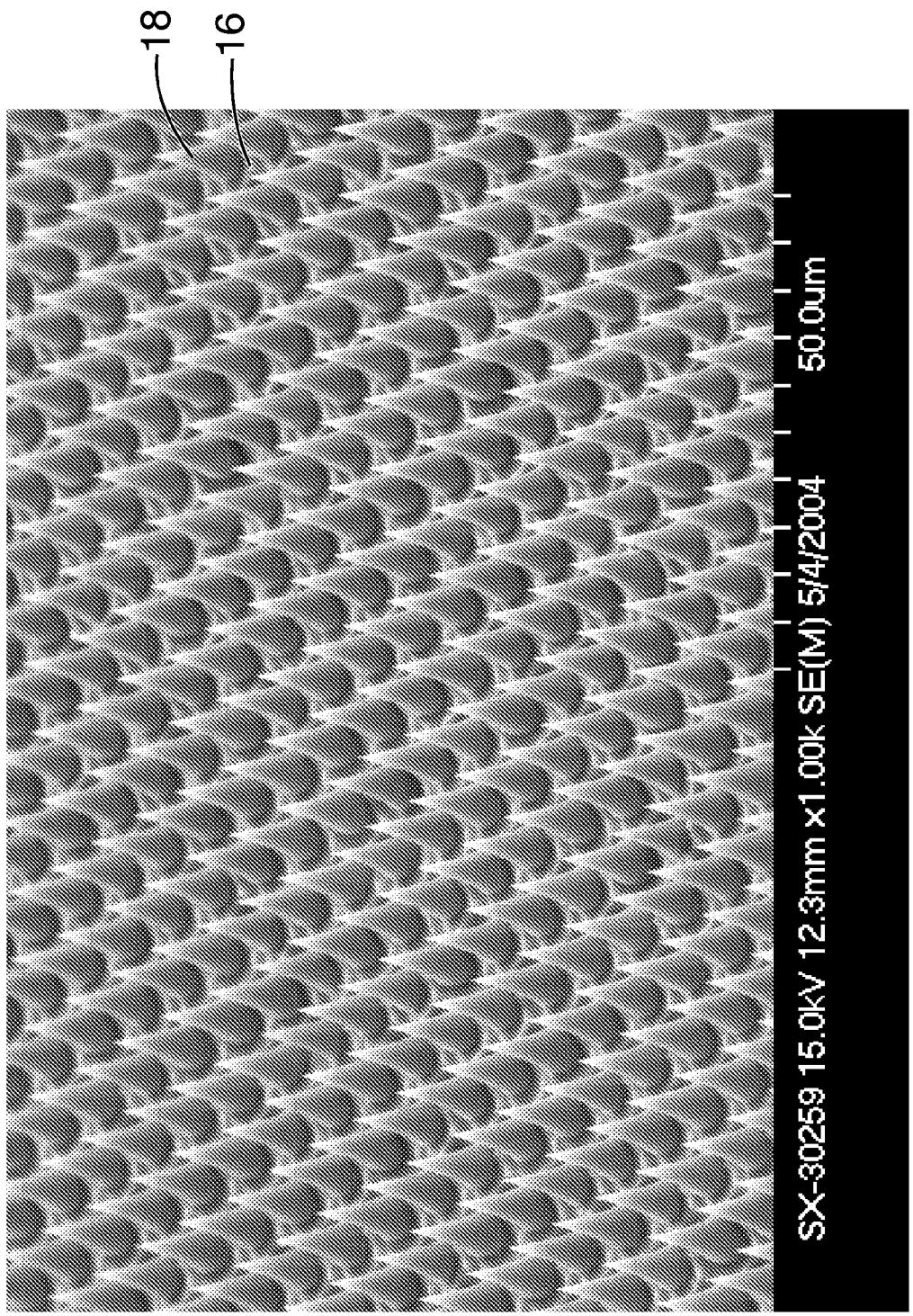
FIG. 6 is an oblique photomicrograph of a spiked glass plate such as that shown in FIG. 5 after etching in accordance with the present invention.
Figure 7:
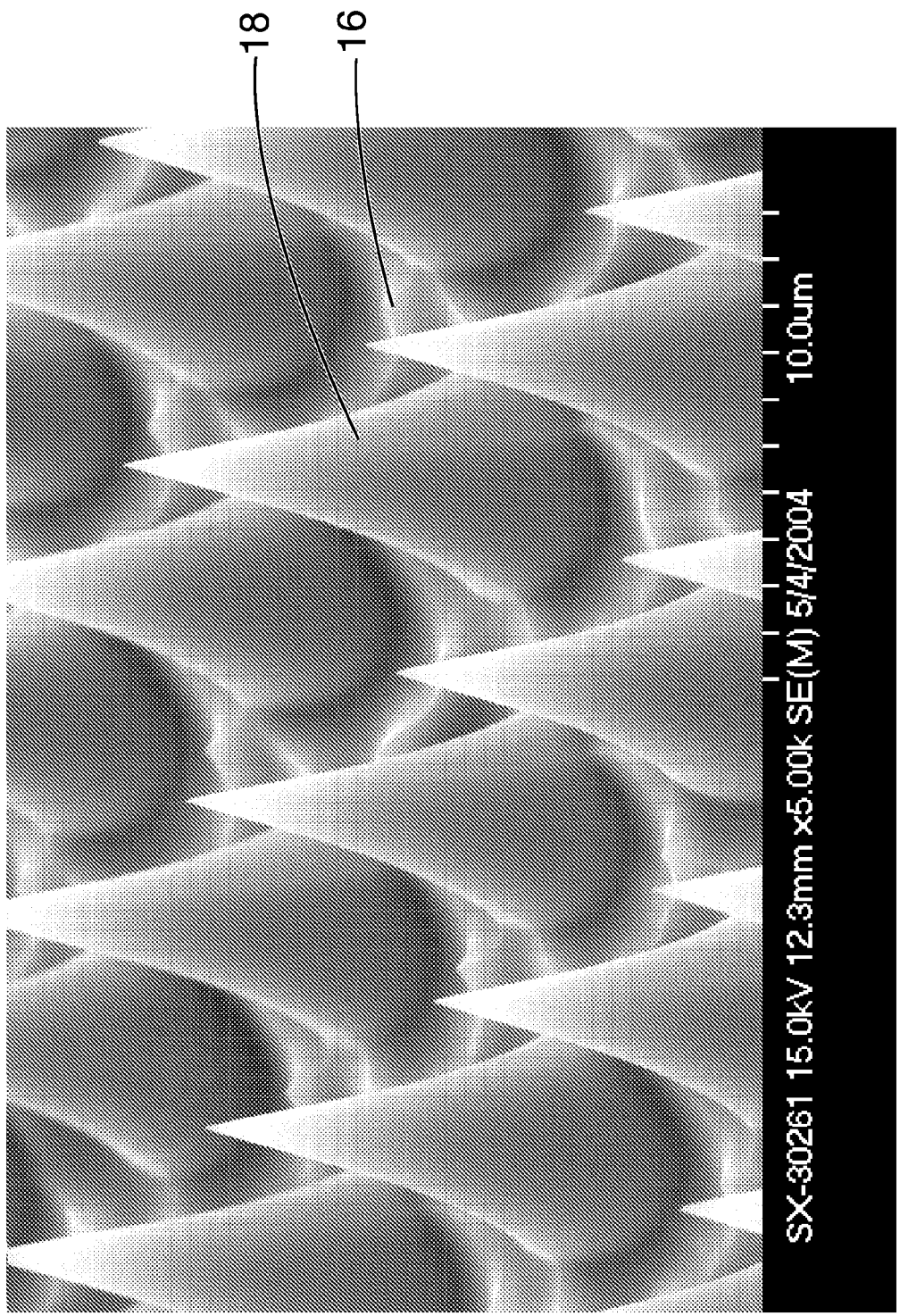
FIG. 7 is an oblique photomicrograph of a spiked glass plate such as that shown in FIG. 6 at a higher magnification.
Figure 8:
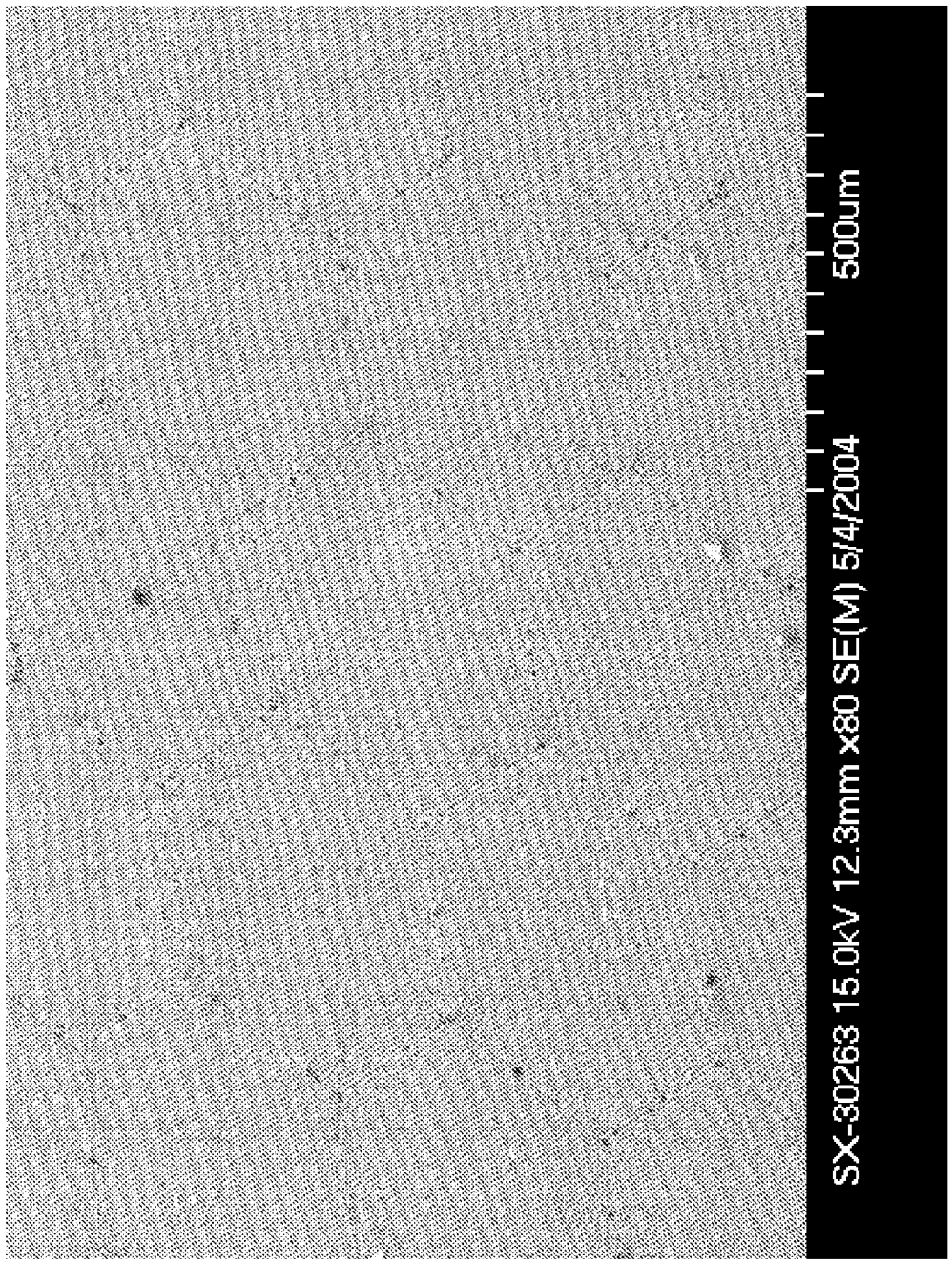
FIG. 8 is an oblique photomicrograph of a spiked glass plate such as that shown in FIG. 6 at a lower magnification.
Figure 9:
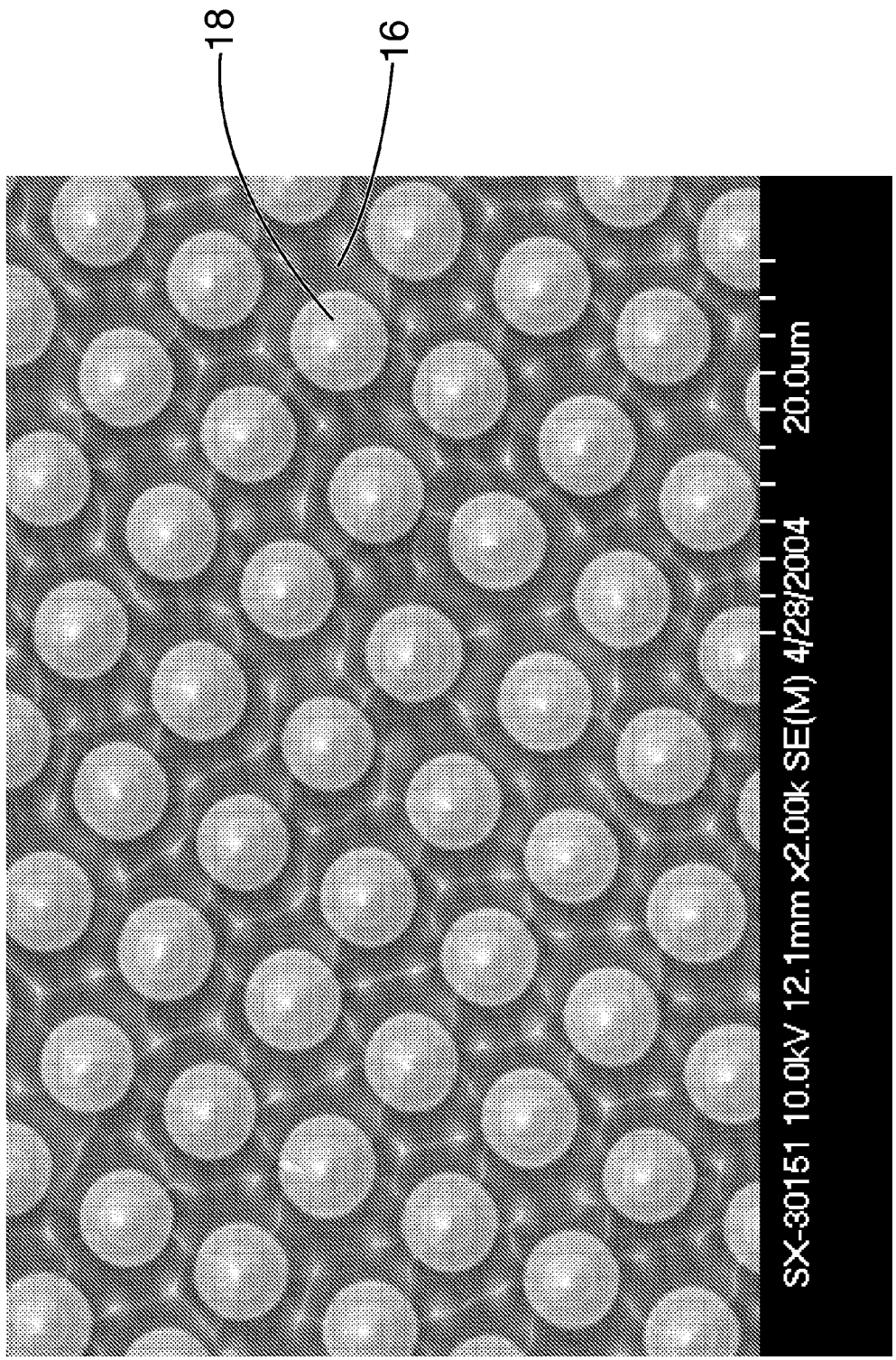
FIG. 9 is a top view photomicrograph of a spiked glass plate such as that shown in FIG. 6 at a higher magnification.
Figure 10:
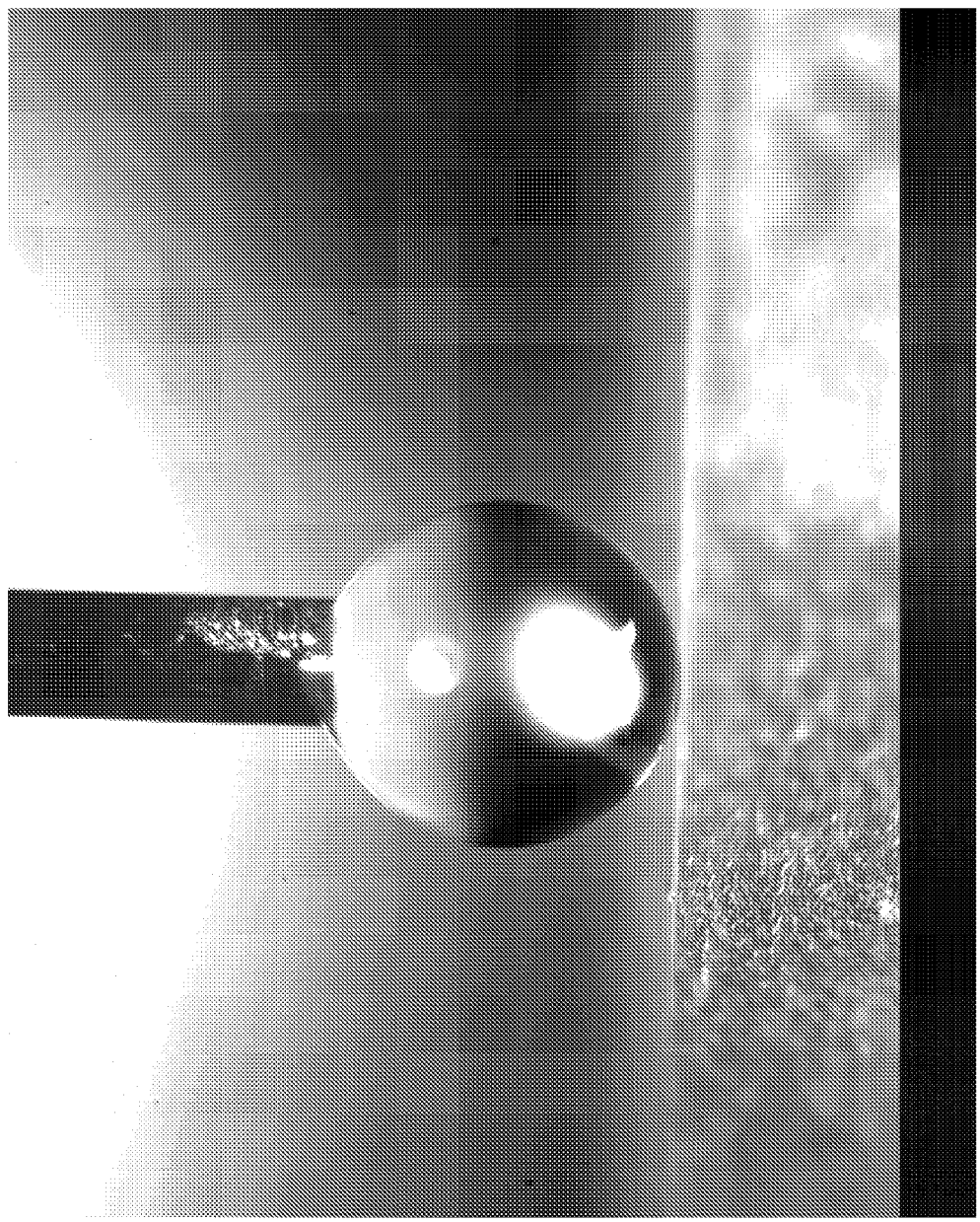
FIG. 10 is a side-view photograph of a drop of water eluted from a syringe onto a super-hydrophobic glass surface in accordance with the present invention.

FIG. 6 is an oblique photomicrograph of a spiked glass plate made in accordance with Example I. The recessive areas 16 and spikes 18 are clearly seen. FIG. 7 shows the spiked glass plate at a higher magnification. FIG. 8 shows the spiked glass plate at a lower magnification, revealing hexagonal patterns of fused bundles. FIG. 9 shows a top-view of the spiked glass plate.

The above described invention has various uses, particularly in the fabrication of super-hydrophobic or super-hydrophilic materials. In general, the sharp surface feature of the present invention amplifies the "phobic" (e.g. hydrophobic) or "philic" (e.g. hydrophilic) interaction of a material and a liquid if at least the protrusive phase is made of or coated with the material. Specifically, a material surface that is naturally repulsive (phobic) to a particular liquid will become super-repulsive to that liquid, whereas a material that is naturally attractive to a particular liquid will become super-attractive to the particular liquid. The present invention therefore has a potential to create a host of new materials to either super-attract or super-repel various liquids, based upon the physical and chemical attributes of the material.

A coating can be applied to the sharply featured surface to enhance or create a super-attractive or super-repellant surface. The coating should be adherent and chemically compatible with the composite base material. A plurality of coatings can be applied. For example, a first coating can serve as a buffer layer to promote compatibility with a functional second coating. There is no limit to the type and number of layers that can be applied to the sharply featured surface. The present invention therefore has a further potential to create a host of new coated materials to either super-attract or super-repel various liquids, based upon the physical and chemical attributes of the material and the coatings.

To create a super-hydrophobic surface, the sharply featured surface may be coated with a hydrophobic material such as a fluorocarbon, for example. The hydrophobic coating may comprise, for example, a coating of PTFE or similar polymer; polymers having $CF_3$ terminal groups are especially suitable. The coating may be spin-coated (applied as a liquid while spinning the material) to obtain a uniform thickness (e.g. Dupont Teflon© AF may be applied in solution). It may also be deposited via a vacuum deposition process. For example, PTFE or other fluorocarbon may be applied by sputtering or hot filament chemical vapor deposition (HFCVD). A self-assembled monolayer is an especially simple and effective hydrophobic coating for various materials, including glass, as it can be applied by simply immersing the material in an appropriate solution, or by pouring or spraying it onto the surface, for example. The surface of a polymer may be fluorinated to make the surface more hydrophobic. Other coatings may be used to make the material hydrophobic and may depend on the materials used in the composite. The result is a coated, super-hydrophobic surface that repels water (including a variety of aqueous fluids).

EXAMPLE II

A spiked disk made in accordance with Example I was immersed in a solution of (tridecafluoro-1,1,2,2 tetrahydrooctyl) trichlorosilane in hexanes to form a self-assembled hydrophobic monolayer on the spiked surface. The resulting disk exhibited super-hydrophobic properties.

A super-hydrophobic disk made in accordance with Example II was tested for super-hydrophobic properties. FIG.

Figure 11:
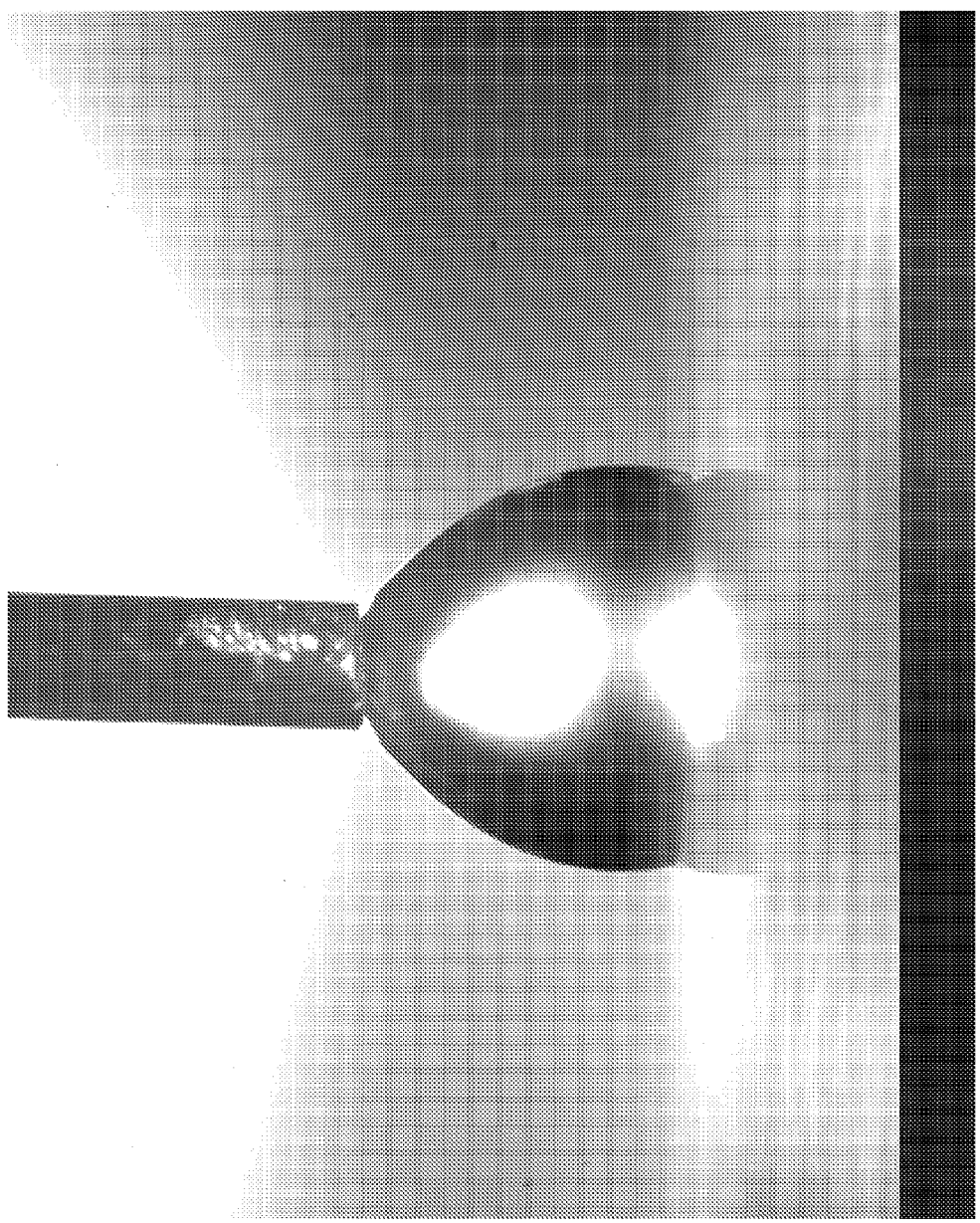
FIG. 11 is a side-view photograph of a drop of water eluted from a syringe onto a flat, hydrophobic-coated glass surface for comparison with the present invention.

10 shows a drop of water eluted from a syringe directly onto the disk. The drop has an apparent contact angle greater than 175°, and approaching 180°. FIG. 11 shows a drop of water eluted from a syringe directly onto a flat, hydrophobic-coated glass surface for comparison with the present invention. The drop has an apparent contact angle of about 105°.

Figure 14:
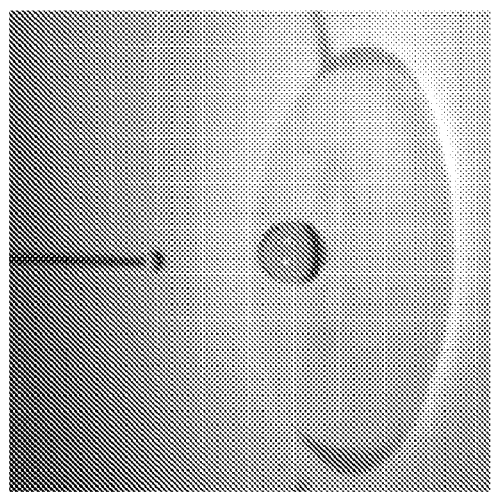
FIG. 14 is a subsequent photographic frame of the drop of water shown in FIG. 13 bouncing off the super-hydrophobic glass surface in accordance with the present invention.
Figure 13:
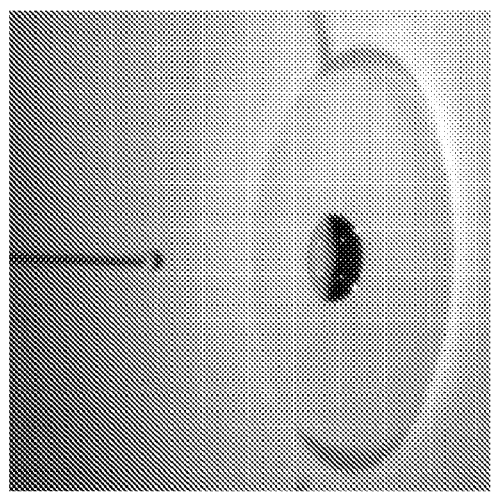
FIG. 13 is a subsequent photographic frame of the drop of water shown in FIG. 12 falling onto and compressing against the super-hydrophobic glass surface in accordance with the present invention.
Figure 12:
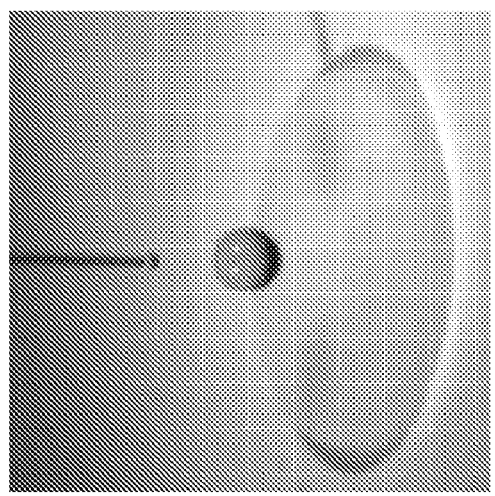
FIG. 12 is a side-view photograph of a drop of water eluted from a syringe and falling toward a super-hydrophobic glass surface in accordance with the present invention.

FIGS. 12-14 are frames excerpted from a motion picture sequence showing a drop of water eluted from a syringe falling toward the super-hydrophobic disk (FIG. 12), falling onto and compressing against the super-hydrophobic disk (FIG. 13), and bouncing upwardly from the super-hydrophobic disk (FIG. 14). The drop of water continued bouncing until it rolled off the surface of the super-hydrophobic disk, leaving the disk completely dry.

Figure 15:
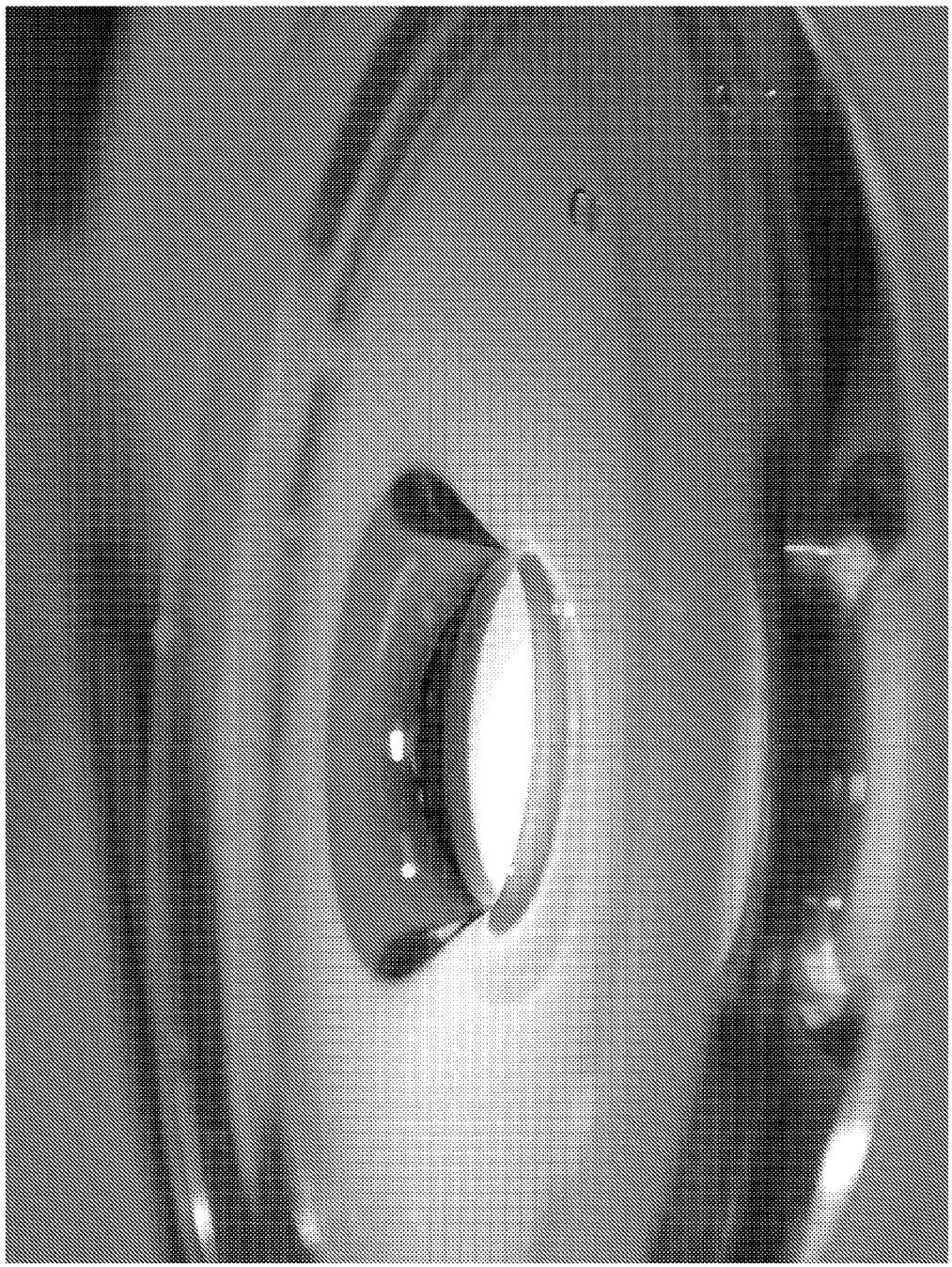
FIG. 15 is an oblique-view photograph of a super-hydrophobic glass disk surrounded by a meniscus of water in accordance with the present invention.

The super-hydrophobic disk was placed on the floor of a Petri dish and water was dropped onto the disk. The water behaved as described above until the water reached a depth approximately 5 mm. The water did not cover the super-hydrophobic disk, but rather formed an annular meniscus thereabout. FIG. 15 shows the super-hydrophobic disk surrounded by a meniscus of water. When sufficient water was added to the Petri dish, the water eventually collapsed over the disk. However, removal of some water and/or placement of a bubble on the disk via a syringe resulted in an immediate return to the condition shown in FIG. 15.

Figure 16:
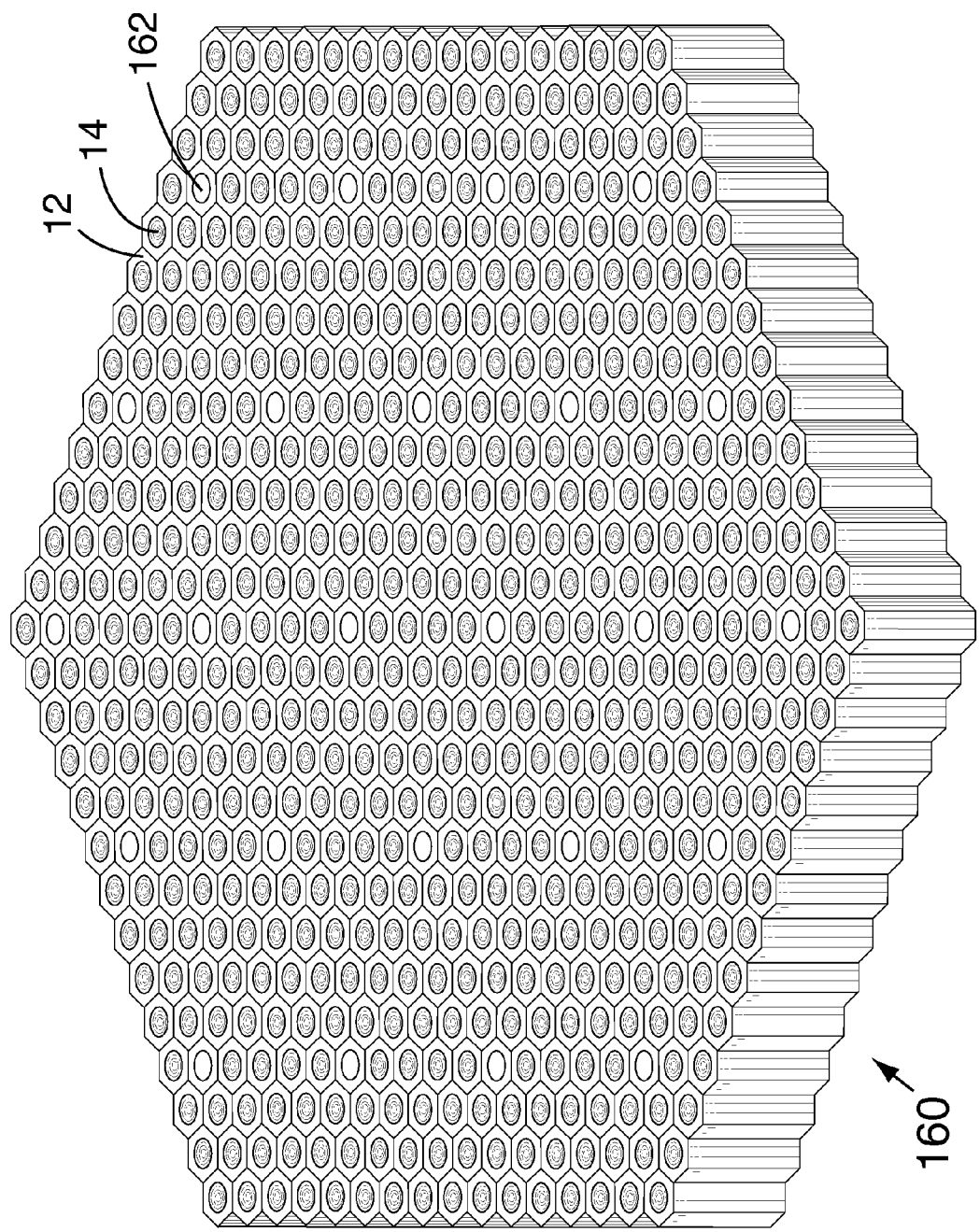
FIG. 16 is a schematic oblique view of a plate similar to that shown in FIG. 5, but with fugitive cores in accordance with the present invention.

In other embodiments of the invention, the composite material may comprise a bundle of more than one kind of composite rod. For example, some of the cores may have a different core phase having a high etchability/solubility (e.g., nano-channel-like cores) so that a perforated product may be fabricated. FIG. 16 shows a plate 160 having all glass rods made of the same matrix glass 12 and most of the rods having the same core glass 14 as described hereinabove. However, some cores are fugitive 162 and are made of a different material. Upon etching of the plate 160, the fugitive cores 162 will dissolve, leaving perforations in the plate 162 while the other cores 14 will produce spikes. The dissolution of the fugitive cores 162 can be complete. Embodiments having perforations has advantages over existing filtering materials in that the present invention can be less susceptible clogging and can therefore be useful for various applications including removal of dissolved gases from various aqueous fluids, and for pressurization of a surface gas layer in various aqueous fluids.

Figure 17:
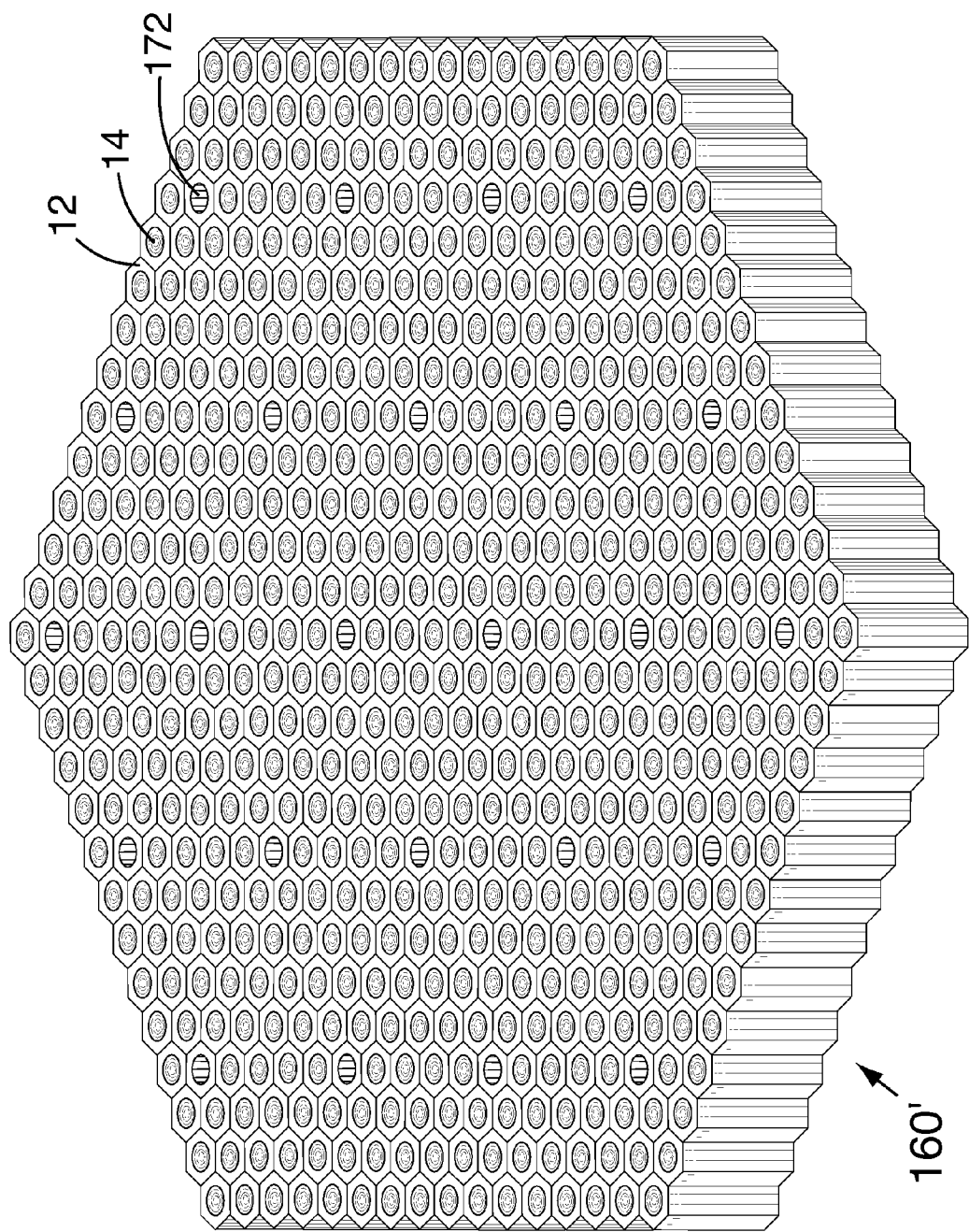
FIG. 17 is a schematic oblique view of a plate similar to that shown in FIG. 16, but with the fugitive cores dissolved away in accordance with the present invention.

The fugitive cores 162 can be made of a material that is soluble in a solvent other than the preselected etchant. For example, the fugitive cores 162 can be made of a polymer that is soluble in acetone. FIG. 17 shows an unetched plate 160' after exposure to a solvent, with perforations 172 where cores 162 have been dissolved away. The plate 160' can then be etched to form spikes of the other cores 14, and most likely, enlargement of the perforations 172. The size of the perforations 172 is ultimately determined by the size of the fugitive cores 162.

In many embodiments of the present invention, the material is preferably produced in tiles for coating and/or laminating a surface. FIG. 5 and other figs. schematically represent tiles or portions of tiles, which can contain millions of spikes or more. Tiles can be bonded to various surfaces such as a watercraft hull or hydrofoil, for example. In order to apply the tiles to irregularly shaped surfaces, unetched tiles can be cut very thin and/or heated to make the tiles became flexible enough to mold to the irregular shape. Once the tiles acquire the proper shape they can then be bonded thereto, and processed (etched and optionally coated). Alternatively, the tiles may be processed first and then bonded to the desired surface.

Figure 18:
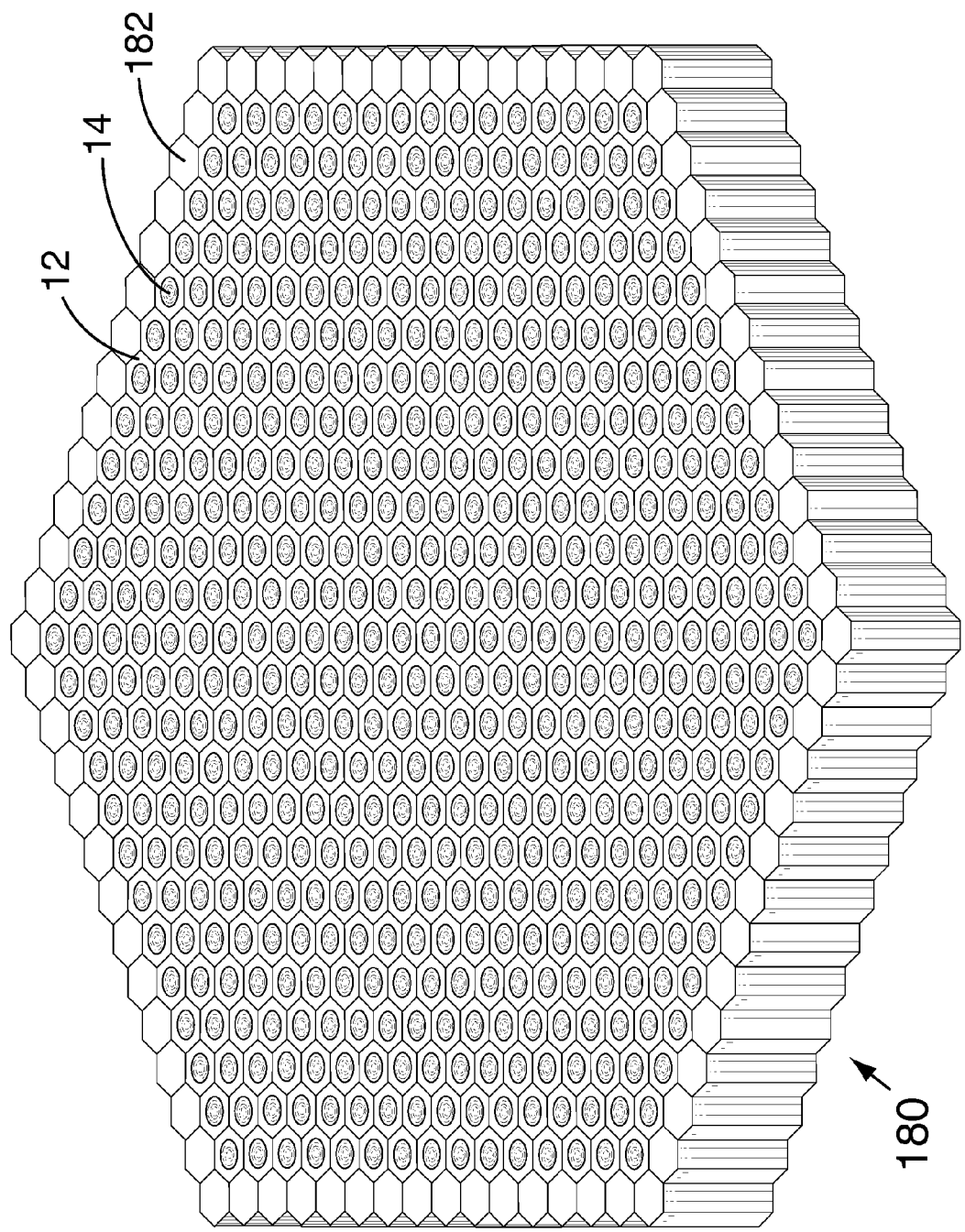
FIG. 18 is a schematic oblique view of a micro-tile having edge rods of fugitive material in accordance with the present invention.

In some embodiments of the present invention, a powdered form of the material is made by producing "micro-tiles" which are very small tiles that appear as powder to the naked eye. Micro-tiles are formed by using a third glass or component which etches quickly compared to the other two components. Referring to FIG. 18, a single micro-tile 180 is formed of rods 12 having cores 14 as described hereinabove. The outermost rods 182 are made of a fugitive material such as highly etchable glass or highly soluble polymer as described hereinabove. As the bundle is drawn, cut, and redrawn, the size of each micro-tile 180 is reduced greatly while the number of micro-tiles 180 in the boule increases greatly. Subsequently, a plate is made which comprises a great number of tiny micro-tiles 180, each having an outline of fugitive rods 182. Upon etching or dissolution, the fugitive rods 182 are etched or dissolved away, releasing all of the individual micro-tiles. Thus a regularly shaped powder is made which can be easily adherently applied to complex surfaces as a coating and/or laminate. This embodiment of the present invention is particularly useful as a super-hydrophobic coating.

Figure 19:
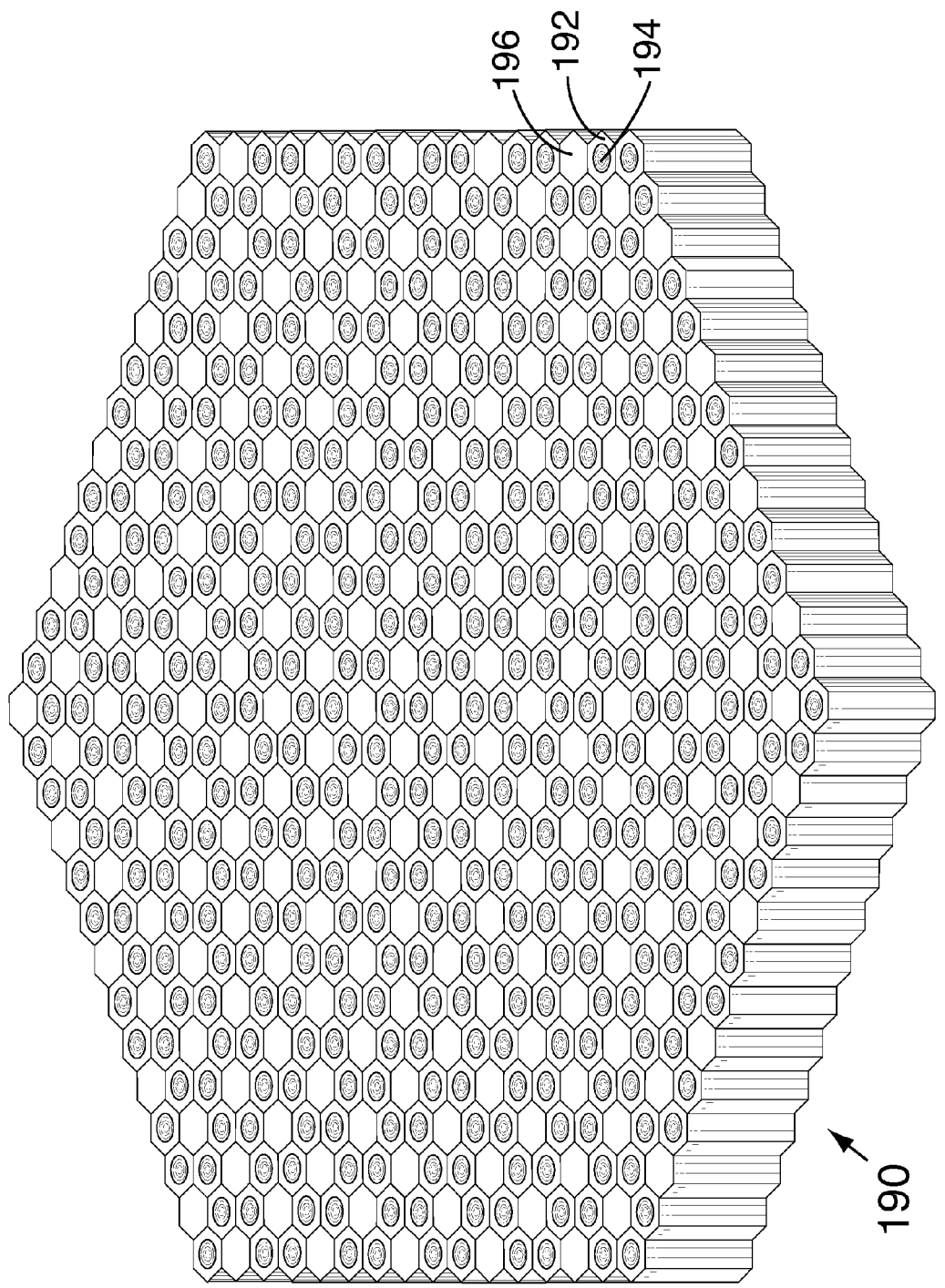
FIG. 19 is a schematic oblique view of a plate having a compound pattern in accordance with the present invention.

In some embodiments of the present invention, particularly in compound arrays of rods, the core material is selected to form the recessive phase, while the matrix material is selected to be the protrusive phase. Such an arrangement can form a spiked surface with a larger fraction of the surface covered by spikes, with less flat, recessive area. Referring to FIG. 19, a plate 190 can comprise solid rods 196 of protrusive phase glass and composite rods having a protrusive glass matrix 192 and a recessive glass core 194. In the particular pattern shown, six composite rods 192/194 encircle each solid rod 196.

Figure 20:
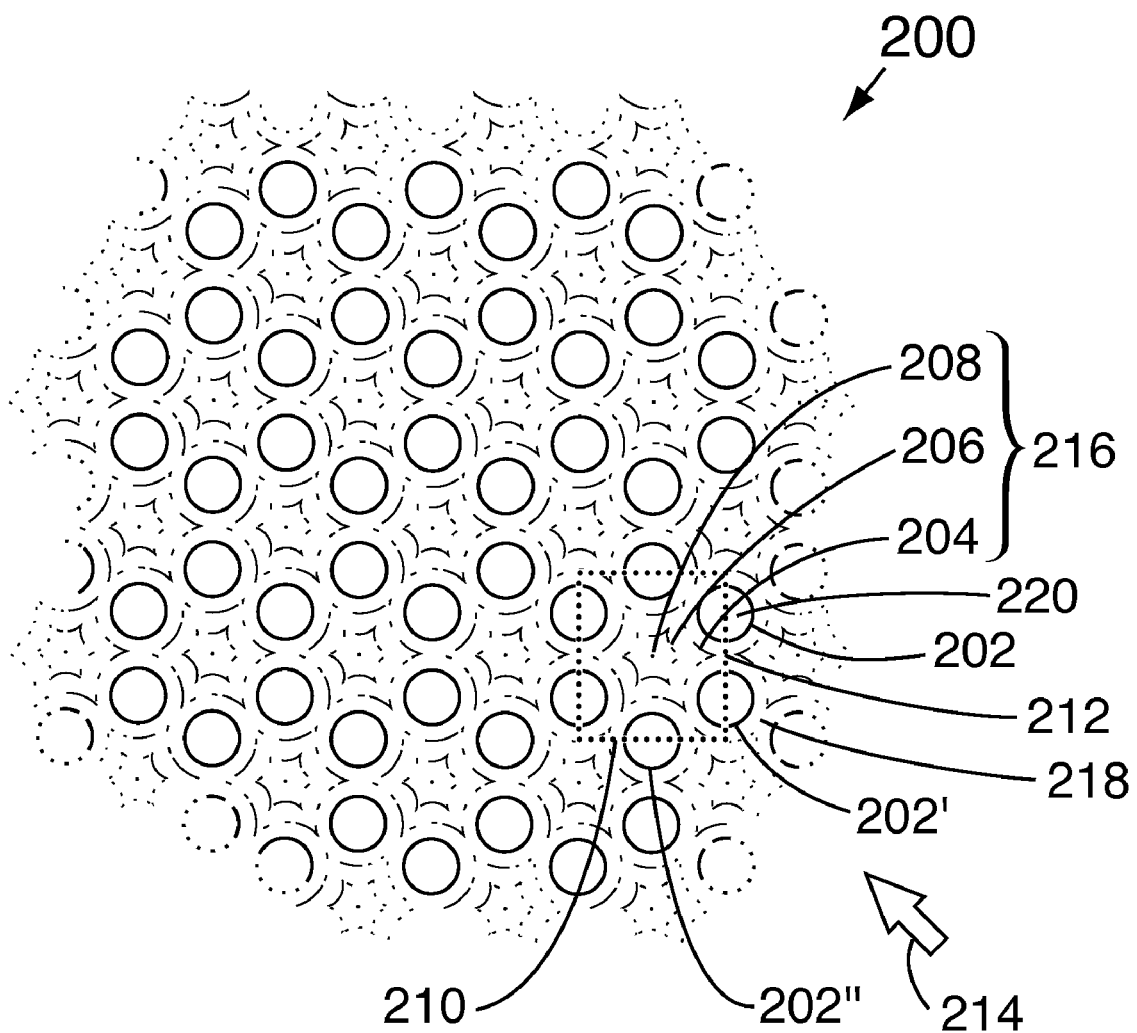
FIG. 20 is schematic, two-dimensional, contour view of a plate showing the results of etching the plate shown in FIG. 19.
Figure 21:
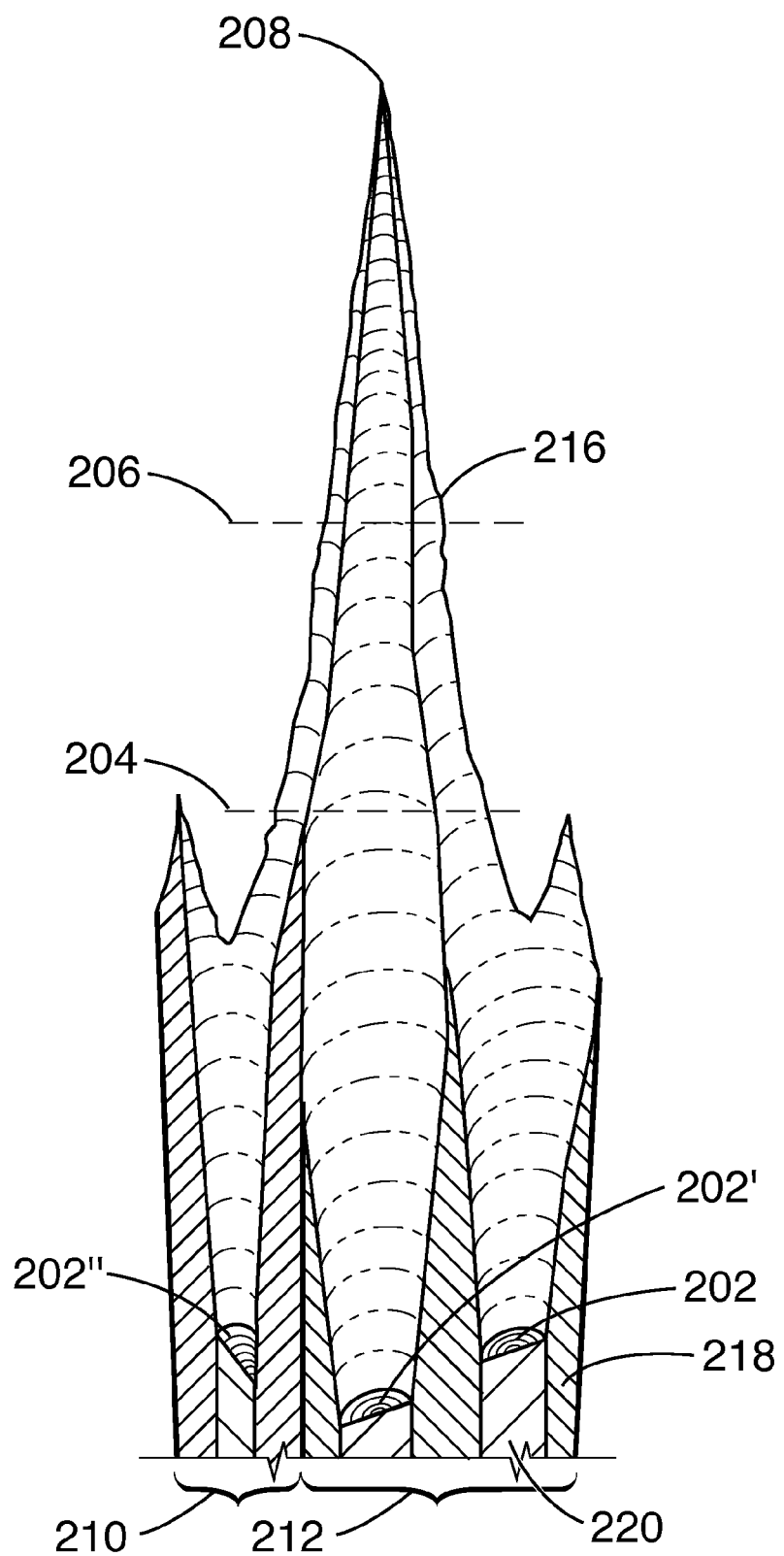
FIG. 21 is schematic side view of a section of the plate shown in FIG. 20.

FIGS. 20, 21 show the results of etching the plate 190 shown in FIG. 19. FIG. 20 shows a portion of the etched plate 200 in a top view showing contour lines of the etched surface features. Recessive phase areas 220 are shown by solid circles 202, 202', 202". Protrusive areas (spikes) 216 are shown by broken contour lines 204, 206 and point 208.

FIG. 21 is a side view of the square section shown in dotted lines in FIG. 20. The perspective of FIG. 21 is from arrow 214 in FIG. 20. The faces of cuts 210 and 212 show sections 202, 202', 202" of recessive phase 220 in the matrix of protrusive phase 218. A spike 216 protrudes through contours 204, 206, and extends to a point 208.

The recessive phase 220 shown in FIGS. 20, 21 can be etched completely away to make a perforated plate 200 that is useful as described herein. Such etching can be carried out simultaneously and/or in a subsequent step with an etchant that does not etch the protrusive phase 218.

Figure 22:
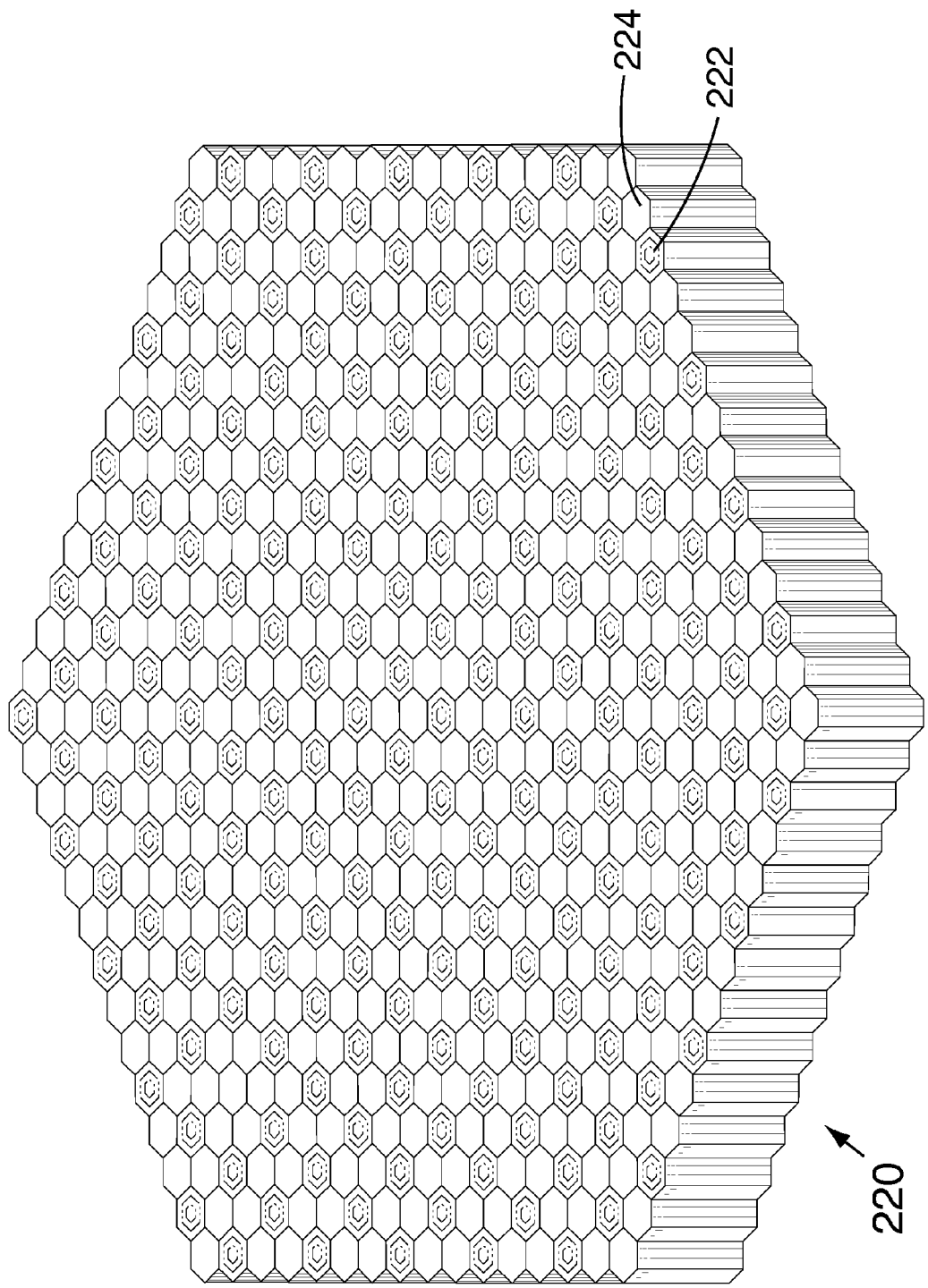
FIG. 22 is a schematic oblique view of a plate having an alternate pattern in accordance with the present invention.

FIG. 22 shows another alternative embodiment of the invention that is similar to that shown in FIG. 19. In FIG. 22, a plate 220 can comprise solid rods 222 of protrusive phase material, each of which is encircled by six solid rods 224 of recessive phase material. A potential advantage of this arrangement is reduced cost of solid rods, with a trade-off in larger recessive areas.

For some applications it may be desirable to bundle different size cores to produce a gradient of spike spacing and/or sizes.

Clearly, many combinations will result in a composite spiked surface. The bundle is a collection of rods which may not be identical and different varieties of rods may be arranged in various patterns.

For some applications it may be desirable to cut the material at an angle other than perpendicular to the drawing direction, resulting in angled spikes that are useful in some directionally sensitive applications.

In some embodiments of the present invention, alternate bundled array shapes, such as square, rectangular, triangle, etc. can be made.

It may be desirable to make an composite spiked surface with electrically conductive (for example, metal) spikes by making micro-channel or nano-channel glass, etching out the cores, filling the holes with metal by electroplating, and then etching back the matrix glass and (more slowly) metal, leaving metal spikes. Thus the metal forms the protrusive phase while the remaining micro-channel glass forms the recessive phase. Suitable metals for include, but are not limited to Au, Ag, Ir, Ni, Pd, Pt, and alloys of any of the foregoing. Conductive spikes can also be made from other micro-channel or nano-channel materials, for example using a conductive polymer.

The electrically conductive spiked surface can be coated with a hydrophobic coating or self-assembled monolayer. The super-hydrophobic properties can be electrically switched on and off, for example by electro-wetting on dielectric (EWOD) or with an electrically switchable surface coating. Another use of composite spikes formed from metal is as electronic field emitters (used as electron emitters for field emission displays, etc.). Electrical contact to the spikes can be made on the bottom (unetched) side of the plate because the conductive cores penetrate through the plate.

The spiked surface can be easily regenerated if it has been damaged. Generally, all that is required is stripping off of the old hydrophobic coating (if necessary), re-etching of the surface to regenerate the sharp features, and reapplication of the hydrophobic coating (if necessary). The base material contains the composite pattern through its thickness (Z-axis), and does not need to be replaced unless it is completely etched away. This is a great advantage since the tiny sharp features may be damaged by scraping.

The composite material can be formed using conventional integrated circuit manufacturing techniques. For example, anisotropic trench etch a suitable first phase (recessive or protrusive) material, fill with second phase material, planarize, and subsequently etch in accordance with the present invention. The matrix material can be disposed on a substrate material, such as only on discrete portions of the substrate. Devices according to the invention can be disposed on chip next to electronic devices, sensors (e.g. MEMS), and the like.

Some advantages of the above described embodiments of the invention include:

1. Materials used in the construction of the surface can be mostly inert or at least non-reactive.
2. Simple acids and/or solvents can be used for the etching step.
3. As compared with the typical photolithography based fabrication, scaled-up production to large quantities of the material is simple and straightforward in most cases.
4. Spiked surface features can be regenerated in-situ quickly and inexpensively if needed.

Applications of the present invention, particularly the super-hydrophobic embodiments thereof, include, but are not limited to the following:

By using a super-hydrophobic, perforated structure (see FIGS. 16, 21 for example), the present invention can be used as a dissolved gas extractor/monitor. The material has a strong resistance to water penetration or even wetting. As pressure or vacuum is used to force water against the material (generally at ambient temperature), the increased energy applied to the liquid becomes sufficient to effect localized, microscopic boiling (vaporization) of the liquid. Any dissolved gases can easily pass through the structure, but not water. The present invention thus provides means of removing and/or sampling for dissolved hazardous gasses (for example, poisonous chemical and/or biological agents) from the water, acting as a filter that is permeable to dissolved gases but impermeable to water. This particular application of the present invention is especially applicable to Homeland Security and the ongoing effort to counter terrorism.

Use of the present invention on watercraft hulls, hydrofoils, and the like significantly reduces frictional drag through water, allowing higher speeds and/or longer range of travel using the same amount of power. The coating/laminate can also be used to reduce the disturbance or wake (i.e. signature) left in the water by the craft. The coating/laminate may be used to reduce or eliminate fouling of hulls by barnacles, dirt, and the like. The coating/laminate can also be used to greatly reduce the corrosive effects of salt water. Thus, the coating/laminate will be advantageous for virtually any water vehicle or device including small water craft, surface ships, submarines, torpedoes, unmanned surface or underwater craft and ocean gliders.

The present invention can be used on moving parts and stators of propellers, turbines, rudders, steering planes, and the like to reduce drag and cavitations, improving the efficiency thereof.

Embodiments of the present invention having electrically conductive spikes that enable EWOD can be used to steer surface and underwater craft. By activating EWOD (selectively switching off the super-hydrophobic properties) on one side of the craft, friction steering will cause the craft to steer in the direction of that side. In underwater craft, the present invention can also be used to control the depth of the craft.

The present invention can be used to make glassware for hazardous and/or precious liquid manipulation. When poured out of glassware made of or coated with the material water and other water based solutions leave no residue and are completely removed from the glassware. An advantage is the elimination of contamination between experiments.

The present invention can be used to make self cleaning glassware, windows, lenses, and the like. The super-hydrophobic material does not leave any residue, but as water and many aqueous solutions roll off the surface, most dust or dirt encountered may be wetted and swept away, thus making the material self cleaning.

The present invention can be used as an anti-condensation appliance. When water vapor condenses on the surface the droplets move to the tips of the coned spikes and roll off the surface very easily. This rolling off generally occurs at the micron to sub-micron level, before any visible appearance of surface fog or frost. Buildup of moisture or ice is eliminated. Applications include, but are not limited to transparent appliances such as, for example, eye glasses, safety goggles, masks, windshields, windows, and the like. The ability of the structured material to be transparent is governed by the laws of optical diffraction. Simply put, when the spike periodicity is much less than an optical wavelength, the structure will appear transparent. This typically occurs, in air, for spike periodicities of less than 300 nm. Moreover, applications include, but are not limited to heat exchangers such as, for example, refrigerators, heat pumps, dehumidifier cooling coils, and the like, thus increasing their energy efficiencies and decreasing or even eliminating the need for a defrost cycle.

The present invention can be used to coat airplane wings, propellers, and the like to keep freezing rain from sticking or accumulating. Such a coating is anti-icing because before water droplets can form ice they drop off the surface.

The present invention can be used as a medium for crystallization. When a water based solution resides on the surface it forms a spherical droplet. When the droplet is allowed to evaporate it will uniformly shrink without pinning to the surface (pinning causes a "coffee stain" ring on most other surfaces). This may be particularly useful for crystallizing ultra-pure proteins, similar to what has been carried out in a micro-gravity environment.

The present invention can be used as a coating for conduits such as pipes, tubing, hoses, and the like, for example. The reduction in viscous drag greatly reduces or eliminates the shearing forces normally associated with laminar flow and turbulence through the conduit. This will cause the entire volume of water to move as a unit with little or no turbulence and thus greatly reduce the amount of energy required to force the fluid therethrough. This is especially true for convection circulation systems where the driving force is weak. The surface properties may also change the conditions under which the flow is turbulent. Since water is in minimal contact with the surface, thermal contact is also decreased, reducing thermal losses of heated and cooled aqueous fluids, and enabling management thereof by strategically locating the coating in the pipes.

The present invention can be used to separate liquids which are immiscible, for example water and oil. The super-hydrophobic material attracts oil and other organic liquids.

With selection of a suitable sharp surface feature and surface properties, the present invention can be used as an anti-clotting surface for blood, which generally will not stick to the surface. Thus, the material prevents blood from clotting thereon, and can be used as a coating for synthetic implants, such as stents, heart valves, artificial heart surfaces, surgical instruments, and for external machines used to circulate blood. The decreased viscous drag on the surface may reduce the shear force on the blood, reducing damage to the blood.

The present invention can be used as a cellular manipulation device that uses a periodic functionalized surface. As an example, specific molecules can be attached to the tip of each glass spike of an uncoated (super-hydrophilic) spiked glass surface. Applications include, for example, DNA/RNA/Protein manipulation and analysis research, and direct injection of cells, for example, for ovum fertilization.

Embodiments of the present invention having metal spikes can be used as field emission devices. The arrayed structure can be caused to emit electrons. Each metal spike can be activated and controlled via the backplane (the composite surface opposite the spiked surface). Since the spike tips can be made exceedingly small (<10 nm), only a small voltage is needed for electron emission. Such a device can be used in display devices or as a substitute for a variety of field emission devices ranging from field emission microscopes to light emitting diodes.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A method of making a super-hydrophobic composite material having sharp surface features comprising the steps of:
    making a fused composite body, said making step comprising:
        forming a bundle comprising a plurality of rods, said bundle comprised of a recessive phase and a protrusive phase, said recessive phase having a higher susceptibility to a preselected etchant than said protrusive phase,
        heating and drawing said bundle to reduce a diameter of said bundle,
        cutting said bundle transversely into sections,
        re-bundling a plurality of sections to form a composite body, and
        fusing the composite body;
    treating a cut surface of said fused composite body with said preselected etchant, wherein said etchant simultaneously etches the recessive and protrusive phases, for a sufficient time so that said protrusive phase protrudes from said fused composite body to form a plurality of sharp surface features having a conical shape, and said recessive phase defines a recessed surface area between said surface features;
    cutting the fused composite body in a transverse direction to form a plate; and
    coating said plurality of sharp surface features with a hydrophobic material,
    wherein a cross sectional area of a tip portion of said coated sharp features is less than 30% of a cross sectional area of a base portion of said sharp features.

2. A method of making a composite material in accordance with claim 1 wherein said recessive phase and said protrusive phase are arranged in an ordered array.

3. A method of making a composite material in accordance with claim 1 wherein said recessive phase comprises a first material selected from the group consisting of glass, metal, ceramic, polymer, and resin;
    and wherein said protrusive phase comprises a second material selected from the group consisting of glass, metal, ceramic, polymer, and resin.

4. A method of making a composite material in accordance with claim 3 wherein said recessive phase comprises a first glass, and wherein said protrusive phase comprises a second glass.

5. A method of making a composite material in accordance with claim 3 wherein said recessive phase comprises a glass, and wherein said protrusive phase comprises a metal.

6. A method of making a composite material in accordance with claim 1 wherein said preselected etchant comprises at least one etchant selected from the group consisting of an organic acid, an inorganic acid, an organic alkali, an inorganic alkali, a polar solvent, a nonpolar solvent, an organic solvent, an inorganic solvent, and mixtures of any of the foregoing.

7. A method of making a composite material in accordance with claim 6 wherein said preselected etchant comprises HF.

8. A method of making a composite material in accordance with claim 1 wherein said preselected etchant comprises a mixed etchant system.

9. A method of making a composite material in accordance with claim 1 wherein said hydrophobic material comprises at least one fluorocarbon.

10. A method of making a composite material in accordance with claim 1, further comprising repeating said steps of (i) heating and drawing, and (ii) cutting, with said re-bundled plurality of sections, at least once.

11. A method of making a composite material in accordance with claim 1, further comprising repeating said steps of (i) heating and drawing, (ii) cutting, and (iii) re-bundling, at least once.

12. A method of making a composite material in accordance with claim 1, wherein a cross sectional area of a tip portion of said sharp features is less than 10% of a cross sectional area of a base portion of said sharp features.

13. A method of making a composite material in accordance with claim 1, wherein a cross sectional area of a tip portion of said sharp features is less than 5% of a cross sectional area of a base portion of said sharp features.

14. A method of making a composite material in accordance with claim 1, wherein sharp features are atomically sharp.

15. A method of making a composite material in accordance with claim 1, wherein each of said surface features comprise a distal end opposite said composite material, integrated with said composite material, and protruding distally from said composite material, each of said surface features reducing in cross sectional area distally from said composite material to provide a lowest cross sectional area at said distal end.

16. A method of making a composite material in accordance with claim 1, further comprising bonding one or more plates comprising sharp surface features to a second surface.

17. A method of making a composite material in accordance with claim 1, further comprising forming a plurality of tiles or micro-tiles comprising sharp surface features from said plate.

18. A method of making a composite material in accordance with claim 1, further comprising bonding more than one plate comprising sharp surface features to a second surface, said second surface and said more than one plate bonded to said second surface forming a composite, said composite having a contact angle greater than 150° with a drop of water.

19. A method of making a composite material in accordance with claim 1, wherein said super-hydrophobic composite has a contact angle greater than 175° with a drop of water.

20. A method of making a composite material in accordance with claim 1, wherein said plurality of sharp surface features are positioned with a periodicity of less than 300 nm.

21. A method comprising
making a composite body comprising a plurality of rods,
wherein some of the rods comprise a recessive phase and a protrusive phase,
wherein the recessive phase has a higher susceptibility to an etchant than the protrusive phase,
wherein one or more groups of rods are surrounded by one or more groups of fugitive rods;
cutting the composite body in a transverse direction to form a plate; and treating a surface of the plate with the etchant so that:
the protrusive phase protrudes from the surface to form a plurality of sharp surface features,
the recessive phase defines a recessed surface area between the surface features, and
the fugitive rods completely dissolve in the etchant, thereby releasing the one or more groups of rods as one or more tiles.

22. The method of claim 21, wherein the one or more tiles are microtiles.

23. The method of claim 21, wherein a plurality of tiles are formed, and the method further comprises coating a surface with a plurality of tiles.

24. The method of claim 21, further comprising coating the plurality of sharp surface features with a hydrophobic material.

* * * * *